United States Patent [19]
Regel et al.

[11] 3,968,120
[45] July 6, 1976

[54] 2-IMIDAZOLYLCARBONYLBENZOIC ACID COMPOUNDS

[75] Inventors: Erik Regel, Wuppertal-Elberfeld; Klaus Lürssen, Koenigsdorf; Karl Heinz Büchel, Wuppertal-Elberfeld, all of Germany

[73] Assignee: Bayer Aktiengesellschaft, Leverkusen, Germany

[22] Filed: Sept. 11, 1972

[21] Appl. No.: 288,229

[30] Foreign Application Priority Data
Sept. 10, 1971 Germany............................ 2145456

[52] U.S. Cl................................... 260/309; 71/92; 71/74; 260/288 R; 260/299; 260/309.2
[51] Int. Cl.².................................... C07D 233/64
[58] Field of Search................. 260/309, 309.2, 299

[56] References Cited
OTHER PUBLICATIONS
Brockmann et al. Chem. Ber. vol. 100, pp. 2890–2893 relied on (1967).
Butler et al. J. Org. Chem. vol. 36, pp. 2542–2547 (1971).
Hein et al. Chem. Abst. vol. 57, column 11203 (1962).
Sarett et al. Chem. Abst. vol. 63, columns 18097–18098 (1965).
Sarges Chem. Abst. vol. 72, No. 66951d (1970).
Staab et al. Chem. Abst. vol. 57, columns 5906–5907 (1962).

*Primary Examiner*—Natalie Trousof
*Attorney, Agent, or Firm*—Burgess, Dinklage & Sprung

[57] ABSTRACT
Certain novel 2-imidazolylcabonylbenzoic acid compounds of the formula:

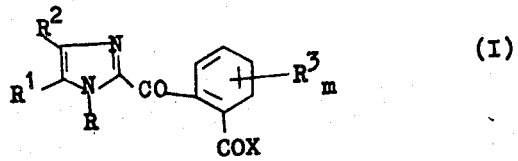

in which
X is hydroxy or metal-oxy or aliphatic hydrocarbyl;
R is hydrogen, alkyl or alkoxyalkyl;
$R_1$ and $R_2$ are hydrogen, alkyl, aryl or halogen (or together represent a fused benzene ring);
m is from 0 to 4, and
$R_3$ is hydrogen, alkyl, alkoxy, nitro, halogen or phenyl;
are outstandingly effective as plant growth regulants to inhibit, stimulate or alter plant growth.

17 Claims, No Drawings

2-IMIDAZOLYLCARBONYLBENZOIC ACID COMPOUNDS

The present invention relates to certain new 2-imidazolylcarbonylbenzoic acid compounds and their esters and salts, to plant-growth regulant compositions containing them and to their use as plant-growth regulators.

It is known that (2-chloroethyl)-trimethylammonium chloride can be used for influencing the growth of plants, particularly of cereals, for example by formation of shorter stems, by prevention of falling down ("lodging"), particularly of wheat, for increasing the berry harvest and for improving frost resistance (see U.S. Pat. No. 3,230,069; French Pat. specification 1,264,886; U.S. Pat. No. 3,156,554; Austrian Pat. No. 222,145; Belgian Pat. No. 673,815; German Pat. No. 1,238,052; and British Pat. No. 944,807).

However, the toxicity of this compound is relatively high. Also, its effectiveness in the case of low applied amounts and concentrations is not always wholly satisfactory.

Furthermore, it is known that phosphoric acid trithiobutyl ester can be used as a plant-growth regulator, in particular as a defoliant (see U.S. Pat. Nos. 3,089,807; 2,943,107 and 2,964,467).

This organophosphorus compound has disadvantages in that it shows, besides a relatively high toxicity, a herbicidal effectiveness that restricts its application to cotton cultivations. Its growth-regulating effect likewise falls off rapidly with low applied amounts and concentrations.

The present invention provides, as new compounds, the 2-imidazolylcarbonylbenzoic acids and their derivatives of the general formula

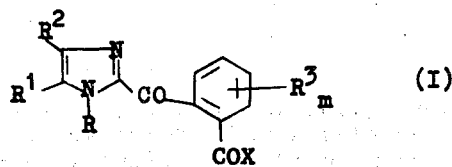

in which
X is hydroxy or a grouping OX', X' being an alkali metal cation (such as sodium, potassium or lithium), an equivalent of an alkaline earth metal cation (such as calcium, magnesium or barium), an equivalent of a heavy metal cation (such as iron, copper, manganese or zinc), or an alkyl, alkenyl, alkynyl, haloalkyl, hydroxyalkyl, alkoxyalkyl or possibly substituted aralkyl radical,
R is hydrogen, alkyl or alkoxyalkyl,
$R^1$ and $R^2$, which may be identical or different, are each, hydrogen, alkyl, aryl or halogen;
or $R^1$ and $R^2$, together with the two carbon atoms in the 4- or 5- positions of the imidazole ring, form a fused benzene ring, which may be substituted by chlorine, nitro or trifluoromethyl,
m is 0, 1, 2, 3 or 4, and
$R^3$ is hydrogen, alkyl, alkoxy, nitro, halogen or phenyl (the phenyl being optionally substituted by halogen, nitro, alkyl, alkoxy or trifluoromethyl), the $R^3$ radicals being identical or different when m is 2, 3 or 4,
and salts thereof, especially those of physiologically compatible acids.

The compounds of the formula (I) and their salts exhibit very good plant-growth-regulating properties.

Preferred compounds of this invention are those in which
$R^1$ and $R^2$ are each hydrogen, straight-chain or branched alkyl with up to 4 carbon atoms (especially methyl) or phenyl, or, together with the 2 carbon atoms in the 4- or 5-positions of the imidazole ring, form a fused benzene ring, which may be substituted by the electronegative substituents chlorine, nitro or trifluoromethyl,
m is 0 or 1;
$R^3$ (if present) is hydrogen, straight-chain or branched alkyl with up to 4 carbon atoms or one of the electronegative substituents nitro, chlorine, bromine or fluorine;
X' is straight-chain or branched alkyl with 1 to 10 carbon atoms (especially of from 1 to 8 carbon atoms), straight-chain or branched alkenyl of from 2 to 6 carbon atoms (especially of from 3 to 6 carbon atoms), straight-chain or branched alkynyl of from 2 to 6 carbon atoms (especially of from 3 to 6 carbon atoms), haloalkyl of from 1 to 3 carbon atoms and 2 to 5 halogen atoms (especially fluorine, chlorine or bromine), for example trichloromethyl or trichloroethyl, straight-chain or branched hydroxyalkyl of from 1 to 4 carbon atoms, alkoxyalkyl of from 1 to 4 carbon atoms in the alkylene moiety (which may be straight-chain or branched) and 1 to 3 carbon atoms in the alkoxy moiety, or aralkyl of from 1 or 2 carbon atoms in the alkylene moiety and 6 to 10 carbon atoms in the aryl moiety, which aryl moiety may be substituted by straight-chain or branched alkyl of from 1 to 4 carbon atoms, haloalkyl of from 1 to 2 carbon atoms and 2 to 5 halogen atoms (especially trifluoromethyl) or the electronegative substituents halogen (especially chlorine), nitro or cyano; and
R is a straight-chain or branched alkyl of from 1 to 4 carbon atoms or alkoxyalkyl of from 1 to 4 carbon atoms in the alkylene moiety (which may be straight-chain or branched) and 1 to 3 carbon atoms in the alkoxy moiety.

The invention also provides a process for the preparation of a 2-imidazolylcarbonylbenzoic acid compound of the formula (I) or a salt thereof, in which
a. an imidazo[1,2-b]isoquinoline-5,10-dione of the general formula

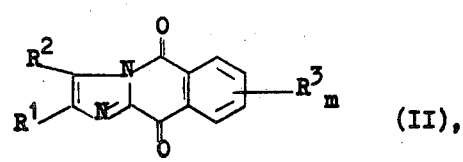

in which $R^1$, $R^2$ and $R^3$ and m have the meanings stated above, is reacted with water or with an alcohol of the general formula

X'OH          (III)

in which $X^1$ is an alkyl, alkenyl, alkynyl, haloalkyl, hydroxyalkyl, alkoxyalkyl or possibly substituted aralkyl radical, in the presence of a base and optionally in the presence of a diluent, the salt that may form being treated, if required, with aqueous acid, or b. a 2-imidazolylcarbonylbenzoic acid derivative of the general formula

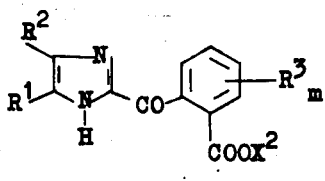

(IV)

in which
 $R^1$, $R^2$, $R^3$ and $m$ have the meanings stated above, and
 $X^2$ is alkyl of from 1 to 3 carbon atoms, namely methyl, ethyl, propyl or isopropyl, is reacted with a haloalkane or haloalkyl alkyl ether of the general formula R—Hal     (V), in which
 R is alkyl or alkoxyalkyl, and
 Hal is halogen, preferably chlorine or bromine, in the presence of an acid-binding agent and optionally in the presence of a diluent, or c. a 2-imidazolylcarbonylbenzoic acid derivative of the general formula

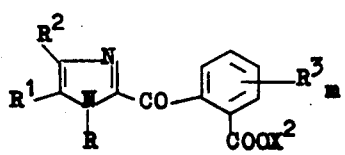

(VI)

in which
 R, $R^1$, $R^2$, $R^3$ and $m$ have the meanings stated above, and
 $X^2$ is alkyl of from 1 to 3 carbon atoms in reacted with an alcohol of the formula (III)
in which $X^1$ is alkyl of from more than 3 carbon atoms, alkenyl, alkynyl, haloalkyl, hydroxyalkyl, alkoxyalkyl or (possibly substituted) aralkyl optionally in the presence of a diluent, or d. a 2-imidazolylcarbonylbenzoic acid derivative of the formula (VI)
in which
 $X^2$ is an alkali metal cation, such as sodium or potassium, and
 R is hydrogen, is reacted with a chloride of the general formula $X^3$Cl     (VII)

in which $X^3$ is an alkaline earth metal cation, such as calcium, barium or magnesium, or a heavy metal cation, such as iron, copper, manganese or zinc, optionally in the presence of a diluent, preferably in water, and in which the compound obtained according to any of the process variants (a) to (d) is converted, if required, into a corresponding salt by any customary method.

Surprisingly, the 2-imidazolylcarbonylbenzoic acids (and their derivatives) according to the invention show a considerably higher plant-growth-regulating activity than the compounds (2-chloroethyl)-trimethylammonium chloride and phosphoric acid trithiobutyl ester, which are known from the prior art and which are the closest active compounds of the same type of activity. The substances according to the invention therefore represent an enrichment of the art.

a. If imidazo[1,2-b]isoquinoline-5,10-dione and methanol are used as the starting materials, the reaction course can be represented by the following equation:

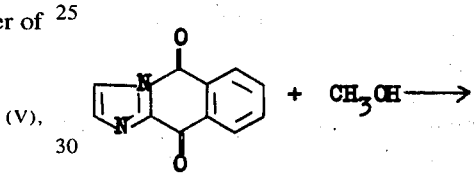

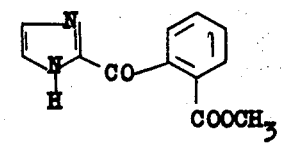

b. If (2-imidazolylcarbonyl)-benzoic acid methyl ester and chloromethyl methyl ether are used as the starting materials, the reaction course can be represented by the following equation:

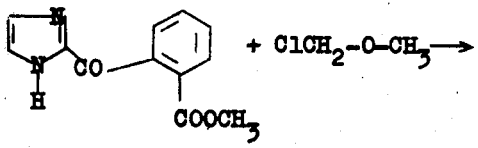

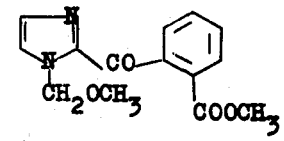

c. If (2-imidazolylcarbonyl)-benzoic acid methyl ester and n-amyl alcohol are used as the starting materials, the reaction course can be represented by the following equation:

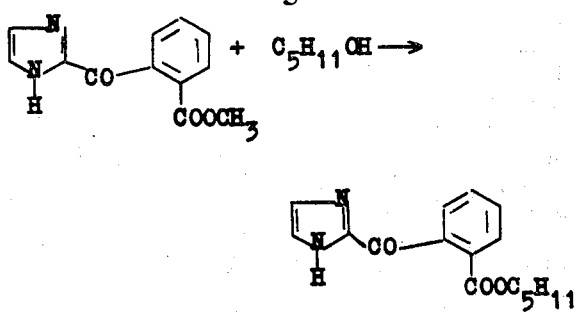

d. If sodium (2-imidazolylcarbonyl)-benzoate and iron (III) chloride are used as the starting materials, the reaction course can be represented by the following equation:

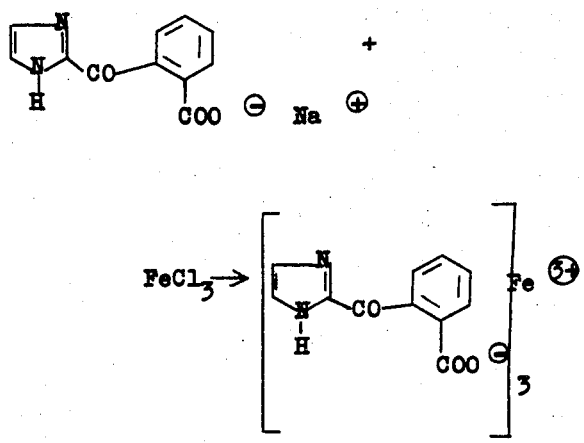

As examples of the imidazo[1,2-b]isoquinoline-5,10-diones (II) that can be used according to the invention, there may be mentioned:

imidazo[1,2-b]isoquinoline-5,10-dione,
2,3-diphenylimidazo[1,2-b]isoquinoline-5,10-dione,
benzimidazo[1,2-b]isoquinoline-5,12-dione,
3-nitrobenzimidazo[1,2-b]isoquinoline-5,12-dione,
2,8-dichlorobenzimidazo[1,2-b]isoquinoline-5,12-dione,
8-nitro-imidazo[1,2-b]isoquinoline-5,10-dione,
9-nitro-imidazo[1,2-b]isoquinoline-5,10-dione,
8-chloro-imidazo[1,2-b]isoquinoline-5,10-dione,
8-bromo-imidazo[1,2-b]isoquinoline-5,10-dione,
8-phenyl-imidazo[1,2-b]isoquinoline-5,10-dione,
2,3,8-triphenyl-imidazo[1,2-b]isoquinoline-5,10-dione,
2-methyl-imidazo[1,2-b]isoquinoline-5,10-dione,
3-methyl-imidazo[1,2-b]isoquinoline-5,10-dione,
7-methoxy-imidazo[1,2-b]isoquinoline-5,10-dione,
2-methyl-7-methoxy-imidazo[1,2-b]isoquinoline-5,10-dione,
3-methyl-7-methoxy-imidazo[1,2-b]isoquinoline-5,10-dione,
2-methoxy-benzimidazo[1,2-b]isoquinoline-5,12-dione,
3-bromo-benzimidazo[1,2-b]isoquinoline-5,12-dione,
2-methyl-8-nitro-imidazo[1,2-b]isoquinoline-5,10-dione,
3-methyl-8-nitro-imidazo[1,2-b]isoquinoline-5,10-dione,
1-nitro-benzimidazo[1,2-b]isoquinoline-5,12-dione,
8-chloro-benzimidazo[1,2-]isoquinoline-5,12-dione,
9-chloro-benzimidazo[1,2-b]isoquinoline-5,12-dione,
8-chloro-3-bromo-benzimidazo[1,2-b]isoquinoline-5,12-dione,
9-chloro-3-bromo-benzimidazo[1,2-b]isoquinoline-5,12-dione,
8chloro-2-methoxy-benzimidazo[1,2-b]isoquinoline-5,12-dione,
9-chloro-2-methoxy-benzimidazo[1,2-b]isoquinoline-5,12-dione,
3-chloro-benzimidazo[1,2-b]isoquinoline-5,12-dione,
8-chloro-1-nitro-benzimidazo[1,2-b]isoquinoline-5,12-dione,
9-chloro-1-nitro-benzimidazo[1,2-b]isoquinoline-5,12-dione,
9-chloro-3-nitrobenzimidazo[1,2-b]isoquinoline-5,12-dione,
8-chloro-3-nitro-benzimidazo[1,2-b]isoquinoline-5,12-dione,
8-trifluoromethyl-benzimidazo[1,2-b]isoquinoline-5,12-dione,
9-trifluoromethyl-benzimidazo[1,2-b]isoquinoline-5,12-dione,
7-tert.-butyl-benzimidazo[1,2-b]isoquinoline-5,12-dione,
8-nitro-benzimidazo[1,2-b]isoquinoline-5,12-dione,
9-nitro-benzimidazo[1,2-b]isoquinoline-5,12-dione,
3-nitro-8-trifluoromethyl-benzimidazo[1,2-b]isoquinoline-5,12-dione,
3-nitro-9-trifluoromethyl-benzimidazo[1,2-b]isoquinoline-5,12-dione,
3-chloro-8-trifluoromethyl-benzimidazo[1,2-b]isoquinoline-5,12-dione, and
3-chloro-9-trifluoromethyl-benzimidazo[1,2-b]isoquinoline-5,12-dione.

The imidazo[1,2-b]isoquinoline-5,10-diones and benzimidazo[1,2-b]isoquinoline-5,12-diones used as starting materials have not been described in the literature but form the subject matter of German published application 2,043,649. They can be prepared by reacting phthalic acid halides with imidazoles or benzimidazoles in the presence of a polar solvent and in the presence of a base.

As examples of the alcohols (III) that can be used according to the invention, there may be mentioned: methyl alcohol, ethyl alcohol, propyl alcohol, isopropyl alcohol, butyl alcohol, isobutyl alcohol, amyl alcohol, iso-amyl alcohol, heptanol, hexanol, octanol, nonanol, decanol, allyl alcohol, vinyl alcohol, trichloroethanol, propynol, butynol, α-hydroxyethanol, β-methoxyethanol, benzyl alcohol, p-nitrobenzyl alcohol, o-chlorobenzyl alcohol, 2-methylbenzyl alcohol, 3-methylbenzyl alcohol, and 3-trifluoromethylbenzyl alcohol.

The alcohols of the formula (III) that can be used according to the invention are known.

As examples of the 2-imidazolylcarbonylbenzoic acid esters (IV) that can be used according to the invention, there may be mentioned:

2-imidazolyl(2')-cabonylbenzoic acid methyl ester,
2-imidazolyl(2')-carbonylbenzoic acid ethyl ester,
2-imidazolyl(2')-carbonyl-4-nitrobenzoic acid methyl ester, 2-imidazolyl(2')-carbonyl-3-nitrobenzoic acid ethyl ester,
2-imidazolyl(2')-carbonyl-5-chlorobenzoic acid methyl ester,
2-imidazolyl(2')-carbonyl-3-chlorobenzoic acid propyl ester,
2-imidazolyl(2')-carbonyl-3-chlorobenzoic acid ethyl ester,
2-imidazolyl(2')-carbonyl-3-chlorobenzoic acid trichloroethyl ester,
2-imidazolyl(2')-carbonyl-5-nitrobenzoic acid ethyl ester,
2-benzimidazolyl(2')-carbonyl-4-nitrobenzoic acid ethyl ester,
2-benzimidazolyl(2')-carbonyl-benzoic acid methyl ester, and
2-(7')-benzimidazolyl(2')-carbonyl-3-chloro-benzoic acid methyl ester.

The 2-imidazolylcarbonylbenzoic acid derivatives of the formula (IV) which can be used according to the invention have not hitherto been described in the literature. They constitute, of course, a sub-class within the formula (I) and therefore they can be prepared according to process variant (a) herein by reacting compounds of the formula

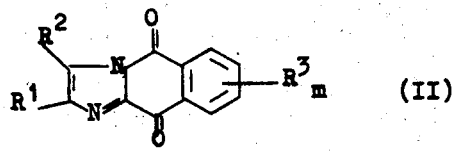

(II)

in which $R^1$ and $R^2$, $R^3$ and $m$ have the meanings stated above with appropriate alcohols of the formula (III), with addition of a base and, optionally, a diluent (see preparative Example 3).

As examples of the haloalkanes or haloalkyl alkyl ethers (V) that can be used according to the invention, there are mentioned:

methyl bromide, ethyl bromide, propyl bromide, chloromethyl methyl ether, chloromethyl ethyl ether, chloromethyl butyl ether, chloroethyl ethyl ether, and chloroethylmethyl ether.

The haloalkanes or haloalkyl alkyl ethers that can be used according to the invention are known or can be prepared according to customary methods.

Furthermore, the starting materials for the process variants (c) and (d), namely the new 2-imidazolyl(2')-carbonylbenzoic acid derivatives of the formula (VI) as defined above, may be prepared according to the process variants (a) and (b) (see preparative Examples 2 and 3) and then reacted with alcohols or solutions containing appropriate cations, for example alkaline earth metal salt solutions or heavy metal salt solutions (see preparative Examples 5, 7 and 8).

Among the anions that can enter into reciprocal reaction with a protonated nitrogen of the 2-imidazolylcarbonylbenzoic acids and their esters of the formula (I), those of physiologically compatible acids are preferred. Examples of such acids are the halogen hydracids, such as hydrochloric acid and hydrobromic acid, especially hydrochloric acid, phosphoric acid, mono- and bi-functional carboxylic acids and hydrocarboxylic acids, such as acetic acid, maleic acid, succinic acid, fumaric acid, tartaric acid, citric acid, salicylic acid, sorbic acid and lactic acid, and 1,5-naphthalenedisulfonic acid.

Inert organic solvents are suitable as diluents in the process variant (a) according to the invention. The preferred solvents are hydrocarbons (which may be chlorinated), such as benzene, chlorobenzene or toluene; ethers, such as diethyl ether, dioxane, or tetrahydrofuran; and nitriles, such as acetonitrile or tolunitrile. The reaction is, however, preferably carried out with an excess of the alcoholic starting material, without any additional diluent.

For ring splitting, a strongly basic reaction solution is required. The basicity can be attained by addition of, for example, an alkali metal alcoholate, alkaline earth metal alcoholate, alkali metal hydroxide or alkaline earth metal hydroxide. Especially suitable are sodium alcoholate, magnesium alcoholate, sodium hydroxide, potassium hydroxide and barium hydroxide.

The reaction temperatures for process variant (a) can be varied within a fairly wide range. In general, the work is carried out at from 0°C to 100°C, preferably from 20°C to 60°C.

When carrying out the process variant (a) there are generally used, for 1 mole of imidazolisoquinoline of the formula (II), 0.1 mole of alkali metal alcoholate, alkaline earth metal alcoholate or sodium, potassium or barium hydroxide and 10 to 20 moles of the alcohol of the formula (III). Further exceeding of the stoichiometric amounts brings no substantial improvement of yield.

If a salt is formed, it may be filtered off, dissolved in water and acidified until a precipitate is obtained; the resultant acid of the formula (I) is isolated by filtration and purified according to customary methods. If an ester is formed in the first instance, it is isolated by filtration and purified according to customary methods.

All polar organic solvents are suitable as diluents in process variant (b) according to the invention. The preferred solvents are halogenated hydrocarbons, such as chlorobenzene, chloroform or carbon tetrachloride; ethers, such as dioxane or tetrahydrofuran; nitrile, such as acetonitrile and tolunitrile; and alcohols, such as methyl alcohol, ethyl alcohol or butyl alcohol.

As the acid-binding agent, any customary acid-binder may be used, especially an alkali metal hydroxide, alkali metal carbonate, alkali metal alcoholate or secondary or tertiary organic base, for example sodium hydroxide, sodium carbonate, sodium ethylate, pyridine or triethylamine. Particularly suitable are sodium ethylate and triethylamine.

The reaction temperature in process variant (b) can be varied within a fairly wide range. In general, the work is carried out from 20°C to 120°C, preferably from 20°C to 100°C.

When carrying out the process variant (b), for 1 mole of the compound of the formula (IV) there are generally used 1 mole of haloalkane or haloalkyl alkyl ether and 1 to, at the most, 2 moles of acid-binder.

To isolate the compound of the formula (I), filtration from the separated halide is effected, the solvent is distilled off in a vacuum, and the oily residue is purified by distillation or crystallization.

As the diluent in the process (c) according to the invention, there is preferably used an excess of the alcoholic starting materials of the formula (III); it is, however, also possible to use inert organic diluents such as hydrocarbons, for example benzene or toluene, ethers, for example diethyl ether or dibutyl ether, and nitriles, for example acetonitrile or tolunitrile.

The reaction temperature in process variant (c) can be varied within a fairly wide range. In general, the work is carried out at from 20°C to 150°C, preferably from 50°C to 150°C.

When carrying out process variant (c), for 1 mole of the compound of the formula (VI) there are generally used from about 10 to 100 moles of the compound of the formula (III). Further exceeding of the stoichiometric amount brings no substantial improvement of yield.

To isolate the compounds of the formula (I) that are obtained according to the process variant (c), the solvent is distilled off down to a small remainder; ether is added to the residue and filtration from the precipitate obtained is effected. The further purification is effected according to customary methods.

All polar solvents are suitable as diluents in the process variant (d), especially alcohols, such as methanol, ethanol or butanol; nitriles, such as acetonitrile; acid amides, such as dimethyl formamide; and sulfoxides, such as dimethyl sulfoxide. The reaction is, however, preferably carried out in aqueous solution.

The reaction temperature can be varied within a fairly wide range. In general, the work is carried out at from 20°C to 100°C, preferably from 20°C to 80°C.

When carrying out the process variant (d), for 1 mole of the compound of the formula (VI) there are generally used 1 to 1.5 equivalents of a cation.

The compounds of the formula (I) are obtained by filtering off the precipitated, sparingly soluble salt.

The active compounds of the formula (I) obtained according to the process variants (a) to (d) can be converted, according to customary methods, into their salts.

The following examples are illustrative of the preparation of the instant invention.

EXAMPLE 1

Preparation of 2-imidazolyl(2')-carbonylbenzoic acid

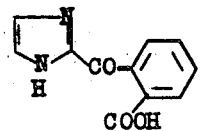

(1)

To a suspension of 19.8 g (0.1 mole) of imidazo[1,2-b]-isoquinoline-5,10-dione in 200 ml of ethanol there was added, with stirring, a solution of 4 g (0.1 mole) of sodium hydroxide in 200 ml of ethanol, and the mixture was heated to 70°C for 1 hour. After cooling to room temperature, the sodium salt formed was filtered off, dissolved in 200 ml of water, the solution was acidified with 100 ml of 30 per cent strength acetic acid, and the precipitate was filtered off.

13 g (60% of the theory) of 2-imidazolyl(2')-carbonylbenzoic acid of the melting point 200°C were obtained.

EXAMPLE 2

Preparation of sodium 2-imidazolyl(2')-carbonylbenzoate

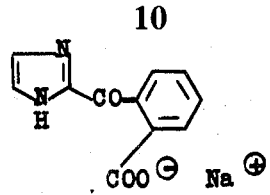

(2)

A solution of 40 g (1 mole) of sodium hydroxide in 1 liter of ethanol was added to a suspension of 198 g (1 mole) of imidazol[1,2-b]-isoquinoline-5,10-dione in 1 liter of ethanol, and the mixture was heated to 70°C for 1 hour, with stirring. After cooling, there were obtained 228.6 g (96% of the theory) of sodium 2-imidazolyl(-2')-carbonylbenzoate of the melting point 200°C, which was obtained by filtration.

EXAMPLE 3

Preparation of 2-imidazolyl(2')-carbonylbenzoic acid methyl ester

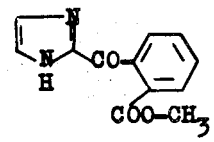

(3)

59.4 g (0.3 mole) of imidazo[1,2-b]-isoquinoline-5,10-dione were suspended, together with 1 g (0.0185 mole) of sodium methylate, in 600 ml of methanol, and the mixture was heated to 80°C for 24 hours, with stirring. After cooling to room temperature, the separated reaction product was filtered off and purified by recrystallization from methanol with the addition of activated charcoal. 59.6 g (81% of the theory) of 2-imidazolyl(2')-carbonylbenzoic acid methyl ester of the melting point 170°C were obtained.

EXAMPLE 4

Preparation of 2-imidazolyl(2')-carbonyl-4-nitrobenzoic acid

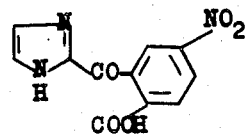

(4)

A solution of 2 g (0.05 mole) of sodium hydroxide in 100 ml of ethanol was added to a suspension of 12.2 g (0.05 mole) of 8-nitro-imidazo-[1,2-b]-isoquinoline-5,10-dione in 200 ml of ethanol, and the reaction mixture was stirred for 1 hour at 70°C. After cooling to room temperature, the sodium salt formed was filtered off, dissolved in 200 ml of water, the solution was acidified with 100 ml of 30 per cent strength acetic acid, and the precipitate was filtered off.

10.2 g (78% of the theory) of 2-imidazolyl(2')-carbonyl-4-nitrobenzoic acid of the melting point 230°C were obtained.

EXAMPLE 5

Preparation of 2-imidazolyl(2')-carbonylbenzoic acid amyl ester

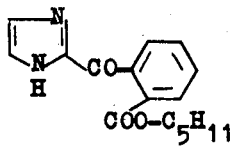

(5)

23 g (0.2 mole) of 2-imidazolyl(2')-carbonylbenzoic acid methyl ester were suspended in 600 ml of hexyl alcohol, and the reaction mixture was heated to 130°C for 1 hour, with stirring. During this time the ester dissolved little by little.

After cooling to room temperature, the excess alcohol was distilled off. The residue was taken up with ether. A crystalline precipitate formed, which was filtered off.

22 g (77% of the theory) of 2-imidazolyl(2')-carbonylbenzoic acid amyl ester of the melting point 120°C were obtained.

EXAMPLE 6

Preparation of 2-imidazolyl(2')-carbonylbenzoic acid isopropyl ester

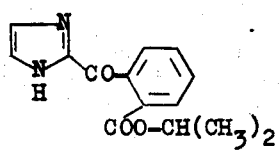

(6)

39.6 g (0.2 mole) of imidazo[1,2-b]isoquinoline-5,10-dione were introduced, with stirring, into a solution of 0.5 g (0.22 mole) of sodium in 1.5 liters of isopropanol, and the reaction mixture was further stirred for 48 hours at 82°C.

Thereafter, cooling was effected and the solvent was distilled off under reduced pressure. The residue was taken up with ethyl acetate; the crystalline precipitate formed was subsequently filtered off.

22.5 g (98.5 % of the theory) of 2-imidazolyl(2')-carbonylbenzoic acid isopropyl ester of the melting point 150°C were obtained.

EXAMPLE 7

Preparation of iron (III) 2-imidazolyl(2')-carbonylbenzoate

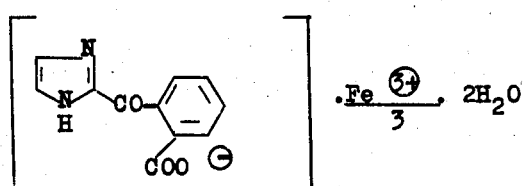

To a solution of 12 g (0.05 mole) of sodium 2-imidazolyl (2')-carbonylbenzoate in 50 ml of water there were added 50 ml of an aqueous solution that contained 3.0 g (0.018 mole) of iron (III) chloride; the reaction mixture was stirred for half an hour at room temperature, and the precipitate formed was filtered off. 7.5 g (55% of the theory) of iron (III) 2-imidazolyl(2')-carbonylbenzoate of the melting point 190°C were obtained.

EXAMPLE 8

Preparation of calcium 2-imidazolyl(2')-carbonylbenzoate

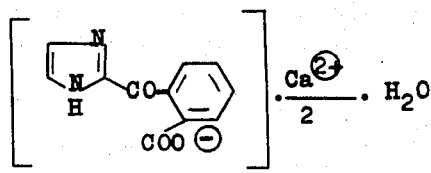

To a solution of 47.8 g (0.2 mole) of sodium 2-imidazolyl-(2')-carbonylbenzoate in 150 ml of water there were added 50 ml of an aqueous calcium chloride solution that contained 11.1 g (0.1 mole) of calcium chloride; the reaction mixture was stirred for half an hour at room temperature, and the precipitated salt was filtered off.

40.2 g (79% of the theory) of calcium 2-imidazolyl(-2')-carbonylbenzoate having a melting point of >250°C were obtained.

EXAMPLE 9

Preparation of 2(1'-methoxymethyl)-imidazolyl(2')-carbonylbenzoic acid methyl ester

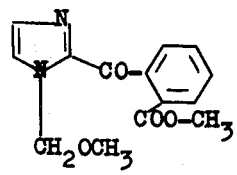

23 g (0.1 mole) of 2-imidazolyl(2')-carbonylbenzoic acid methyl ester were slowly introduced into a solution of 2.3 g (0.1 mole) of sodium in 200 ml of ethanol. The suspension obtained was stirred for 1 hour at room temperature; thereafter, the solvent was distilled off to dryness and the crystalline residue obtained was suspended in 300 ml of acetonitrile. To this suspension there were added dropwise at room temperature, with stirring, 8 g (0.1 mole) of chloromethyl methyl ether; further stirring was subsequently effected for 3 days at room temperature. Sodium chloride separated, which was removed by filtration. The clear solution was distilled off from the solvent, the oily residue was taken up with benzene and water, and the organic phase was separated. This was washed several times with water, dried over sodium sulfate and distilled in a vacuum. There were obtained 12 g (78% of the theory) of 2-(1'-methoxymethyl)-imidazolyl(2')-carbonylbenzoic acid methyl ester of the boiling point 170°C/0.3 mm Hg and refractive index $n_D^{20}$ of 1.5675.

The compounds in the following Table are prepared by methods analogous to those described in Examples 1 to 9.

Table 1

| Example Number | R | R¹ | R² | R³$_m$ | X | Melting point °C, Boiling point °C/mm Hg |
|---|---|---|---|---|---|---|
| 10 | $CH_3$ | H | H | 3-$NO_2$ | $OC_2H_5$ | 118 |
| 11 | $CH_3OCH_2$ | H | H | H | $OCH_3$ | Hydrochloride |
| 12 | H | H | H | H | $OC_8H_{17}$ | 128 |
| 13 | H | H | H | H | $OCH_2-CH=CH_2$ | 114 |
| 14 | H | H | H | H | $OC_4H_9$ | 116 |
| 15 | H | H | H | H | $O^-]\tfrac{1}{2}Ba^{2+}$ | >250 |
| 16 | H | H | H | H | $O^-]\tfrac{1}{2}Zn^{2+}$ | >250 |
| 17 | $CH_3$ | H | H | H | $OC_2H_5$ | 0.5/170 |
| 18 | H | H | H | H | $OC_2H_5$ | 170 |
| 19 | H | H | H | H | $O^-K^+$ | 200 |
| 20 | H | H | H | H | $O^-]\tfrac{1}{2}Mn^{2+}$ | >250 |
| 21 | H | H | H | H | $O^-]\tfrac{1}{2}Cu^{2+}$ | >250 |
| 22 | H | H | H | H | $OC_6H_{11}$ | 114 |
| 23 | H | H | H | H | $O^-]\tfrac{1}{2}Mg^{2+}$ | >250 |
| 24 | H | H | H | H | $OCH_2-CH(CH_3)_2$ | 120 |
| 25 | H | H | H | 4-$NO_2$ | $OCH_3$ | 120 |
| 26 | H | H | H | H | $OC_3H_7$ | 140 |
| 27 | H |  | | H | OH | 250 |
| 28 | H | H | $CH_3$ | H | $OCH_3$ | 170 |
| 29 | $CH_3$ | H | H | H | $OCH_3$ | 82 |
| 30 | H |  | | 4-$NO_2$ | OH | 280 |

The compounds of formula (I) have pronounced plant-growth affecting properties. As especially effective plant-growth-regulating substances, there may be mentioned:

2-imidazolyl(2')-carbonyl-benzoic acid,
sodium 2-imidazolyl(2')-carbonyl-benzoate,
2-imidazolyl(2')-carbonyl-benzoic acid methyl ester,
2-imidazolyl(2')-carbonyl-4-nitro-benzoic acid,
2-imidazolyl(2')-carbonyl-benzoic acid amyl ester,
2-imidazolyl(2')-carbonyl-benzoic acid isopropyl ester,
iron 2-imidazolyl(2')-carbonyl-benzoate,
calcium 2-imidazolyl(2')-carbonyl-benzoate,
2-(1'-methoxymethyl)-imidazolyl(2')-carbonyl-benzoic acid methyl ester and its hydrochloride,
2-(1'-methyl)-imidazolyl(2')-carbonyl-3-nitro-benzoic acid ethyl ester,
2-imidazolyl(2')-carbonyl-benzoic acid octyl ester,
2-imidazolyl(2')-carbonyl-benzoic acid allyl ester,
2-imidazolyl(2')-carbonyl-benzoic acid butyl ester,
barium 2-imidazolyl(2')-carbonyl-benzoate,
zinc 2-imidazolyl(2')-carbonyl-benzoate,
2-(1'-methyl)-imidazolyl(2')-carbonyl-benzoic acid ethyl ester,
2-imidazolyl(2')-carbonyl-benzoic acid ethyl ester,
potassium 2-imidazolyl(2')-carbonyl-benzoate,
manganese 2-imidazolyl(2')-carbonyl-benzoate,
copper 2-imidazolyl(2')-carbonyl-benzoate,
2-imidazolyl(2')-carbonyl-benzoic acid hexyl ester,
magnesium 2-imidazolyl(2')-carbonyl-benzoate,
2-imidazolyl(2')-carbonyl-benzoic acid isobutyl ester,
2-imidazolyl(2')-carbonyl-4-nitro-benzoic acid methyl ester, and
2-imidazolyl(2')-carbonyl-benzoic acid propyl ester.

The active compounds according to the invention interfere with the physiological phenomena of plant growth and can therefore be used as plant-growth regulators.

The different effects of the active compounds depend essentially on the point in time of the application, with reference to the development stage of the seed or the plant, as well as on the concentrations applied.

Plant-growth regulators are used for various purposes which are connected with the development stage of the plant.

With the substances according to the invention the growth of plants can be strongly inhibited. This growth inhibition is of interest in the case of grasses in order to reduce the frequency of grass-cutting. An inhibition of the vegetative growth plays an important part in the case of cereals, too, since lodging can hereby be lessened or completely prevented.

In the case of may cultivated plants, the inhibition of vegetative growth permits a denser planting of the cultivation so that a yield increase with reference to the soil area can be attained. A further mechanism of yield increase with growth inhibitors is based on the fact that the nutrients benefit to an increased extent the blossom formation and fruit formation, while the vegetative growth is restricted.

During the growth of the plant, the lateral branching too can be multiplied by a chemical breaking of the apical dominance. In this there is interest, for instance, in the case of the propagation of plants by cuttings. In a concentration-dependent manner, however, it is also possible to inhibit the growth of side-shoots, for example in order to prevent in tobacco plants the formation of side-shoots after decapitation and thus to promote the leaf growth.

The influence of the active compounds on the foliage of the plants can be so regulated that a defoliation is achieved in order, for example to facilitate the harvested or to reduce transpiration at a time at which the plant is to be transplanted.

Under certain conditions, the premature fall of fruits can be prevented or the fruit fall can be promoted up to a certain extent in the sense of a chemical thinning out. The promotion of the fruit fall can, however, also be so exploited that the treatment is effected at the time of the harvest, whereby a facilitation of harvesting occurs.

With the active compounds it can also be achieved that the shooting of buds or the germination of seeds is retarded, for example in order to avoid damage by late frosts in frost-hazarded areas.

The active compounds according to the present invention can be converted into the usual formulations, such as solutions, emulsions, suspensions, powders, pastes and granulates. These may be produced in known manner, for example by mixing the active compounds with extenders, that is liquid or solid or liquefied gaseous diluents or carriers, optionally with the use of surface-active agents, that is, emulsifying agents and/or dispersing agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include nonionic and anionic emulsifers, such as polyoxyethylene-fatty acid esters, polyoxyethylene-fatty alcohol ethers, for example alkylarylpolyglycol ethers, alkyl sulfonates, alkyl sulfates and aryl sulfonates; and preferred examples of dispersing agents include lignin, sulfite waste liquors and methyl cellulose.

The active compounds according to the invention may be present in the formulations in admixture with other active compounds.

The formulations contain, in general, from 0.1 to 95, preferably from 0.5 to 90, per cent by weight of active compound.

The active compounds may be applied as such, in the form of their formulations or of the application forms prepared therefrom, such as ready-to-use solutions, emulsions, suspensions, powders, pastes and granulates. Application takes place in the usual manner, for instance by watering, spraying, atomising, scattering or dusting.

The amount of active compound used may vary within fairly wide ranges. It depends essentially on the nature of the desired effect. In general, the applied amounts are from 0.01 to 100 kg/hectare, preferably from 0.1 to 10 kg/hectare.

The present invention also provides a plant-growth-regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants, which comprises applying to the plants or to a habitat thereof a compound of the present invention alone or in the form of a composition containing as active ingredient a compound of the present invention in admixture with a diluent or carrier. The present invention further contemplates methods of providing plants the growth of which has been regulated by their being grown in areas in which immediately prior to and/or during the time of the growing a compound of the present invention was applied alone or in admixture with a diluent or carrier.

In the following Examples, some activities of the substances according to the invention as growth regulators are shown, without thereby excluding the possibility of further application as growth regulators. The active compounds of this invention are identified by the numbers of the corresponding preparative Examples given hereinafter.

EXAMPLE A

Defoliant activity in bean plants

Solvent: 10 parts by weight methanol
Emulsifier: 2 parts by weight polyethylene sorbitan monolaurate To produce a suitable preparation of active compound, 1 part by weight of active compound was mixed with the stated amounts of solvent and emulsifier, and water was added until the desired concentration was reached.

Young bean plants about 15 cm high, the primary leaves of which are fully formed, were sprayed with the preparation of active compound until dripping wet. After 8 days, the plant-physiological effect was evaluated.

The active compounds, the concentrations of the active compounds and the results can be seen from the following Table A.

Table A

| Defoliant activity in bean plants | | |
|---|---|---|
| Active compound (Example No.) | Concentration in ppm | Defoliation in % |
| $O=P(SC_4H_9)_3$ | 1000 | 50 |
| | 500 | 20 |
| (known) | 250 | 0 |
| 1 | 1000 | 100 |
| | 500 | 100 |
| 2 | 1000 | 100 |
| 3 | 1000 | 100 |
| | 500 | 100 |
| 5 | 1000 | 100 |

Table A-continued

| Active compound (Example No.) | Defoliant activity in bean plants Concentration in ppm | Defoliation in % |
| --- | --- | --- |
|  | 500 | 80 |
| 6 | 1000 | 100 |
|  | 500 | 80 |
| 7 | 1000 | 100 |
| 8 | 1000 | 100 |
| 11 | 1000 | 100 |
|  | 500 | 80 |
|  | 250 | 80 |
| 13 | 1000 | 100 |
|  | 500 | 100 |
| 14 | 1000 | 100 |
|  | 500 | 100 |
| 15 | 1000 | 100 |
|  | 500 | 80 |
| 18 | 1000 | 100 |
|  | 500 | 100 |
|  | 250 | 100 |
| 19 | 1000 | 100 |
| 20 | 1000 | 100 |
| 22 | 1000 | 100 |
|  | 500 | 100 |
|  | 250 | 20 |
| 23 | 1000 | 100 |
|  | 500 | 100 |
|  | 250 | 80 |
| 24 | 1000 | 100 |
|  | 500 | 100 |
| 26 | 1000 | 100 |

EXAMPLE B

Growth inhibition in wheat

Solvent: 10 parts by weight methanol
Emulsifier: 2 parts by weight polyethylene sorbitan monolaurate To produce a suitable preparation of active compound, 1 part by weight of active compound was mixed with the stated amounts of solvent and emulsifier, and water was added until the desired concentration was reached.

Young wheat plants 5–8 cm high were sprayed with the preparation of active compound until dripping wet. After 14 days, the growth increase was measured and the growth inhibition was calculated as a percentage of the growth increase of the control plants.

The active compounds, the concentrations of the active compounds and the results can be seen from the following Table B.

Table B

| Active compound (Example No.) | Growth inhibition in wheat Concentration in ppm | Inhibition in % |
| --- | --- | --- |
| $ClCH_2-CH_2-N^+(CH_3)_3Cl^-$ | 1000 | 35 |
|  | 500 | 15 |
| (known) |  |  |
| 3 | 1000 | 50 |
|  | 500 | 15 |
| 11 | 500 | 40 |
| 12 | 500 | 30 |
| 13 | 500 | 35 |
| 14 | 500 | 45 |
| 18 | 500 | 15 |
| 22 | 500 | 20 |

EXAMPLE C

Growth inhibition in bean plants

Solvent: 10 parts by weight methanol
Emulsifier: 2 parts by weight polyethylene sorbitan monolaurate To produce a suitable preparation of active compound, 1 part by weight of active compound was mixed with the stated amounts of solvent and emulsifier, and water was added until the desired concentration was reached.

Young bean plants about 10 cm high were sprayed with the preparation of active compound until dripping wet. After 14 days, the growth increase was measured and the growth inhibition was calculated as a percentage of the growth increase of the control plants.

The active compounds, the concentrations of the active compounds and the result can be seen from the following Table C.

Table C

| Active compound (Example No.) | Growth inhibition in bean plants Concentration in ppm | Growth inhibition in % |
| --- | --- | --- |
| $ClCH_2-CH_2-N^+(CH_3)_3Cl^-$ | 1000 | 35 |
|  | 500 | 25 |
| (known) | 250 | 10 |
| 4 | 1000 | 60 |
|  | 500 | 40 |
|  | 250 | 20 |
| 9 | 1000 | 100 |
|  | 500 | 80 |
|  | 250 | 35 |
| 10 | 1000 | 75 |
|  | 500 | 50 |
|  | 250 | 50 |
| 16 | 1000 | 80 |
|  | 500 | 40 |
|  | 250 | 25 |
| 17 | 1000 | 80 |
|  | 500 | 40 |
|  | 250 | 20 |
| 21 | 1000 | 50 |
|  | 500 | 50 |
|  | 250 | 50 |
| 25 | 1000 | 50 |
|  | 500 | 50 |
| 27 | 500 | 35 |

It will be understood that the specification and examples are illustrative but not limitative of the present invention and that other embodiments within the spirit and scope of the invention will suggest themselves to those skilled in the art.

What is claimed is:

1. 2-Imidazolylcarbonylbenzoic acid compound of the formula:

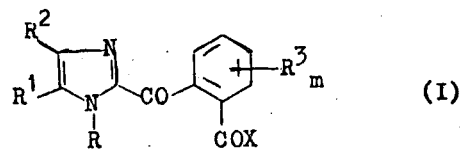

in which
X is hydroxy or OX', X' being
a. an alkali metal cation,
b. an equivalent of an alkaline earth metal cation or an equivalent of a metal cation selected from the group consisting of iron, copper, manganese and zinc, or
c. alkyl of from 1 to 10 carbon atoms, alkenyl of from 2 to 6 carbon atoms, alkynyl of from 2 to 6 carbon atoms, haloalkyl of from 1 to 3 carbon atoms and 2 to 5 halogen atoms, hydroxyalkyl of from 1 to 4 carbon atoms, alkoxyalkyl of from 1 to 4 carbon atoms in the alkylene moiety and 1 to 3 carbon atoms in the alkoxy moiety, or aralkyl of from 1 to 2 carbon atoms in the alkylene moiety and 6 to 10 carbon atoms in the aryl moiety;

R is hydrogen or alkyl or alkoxyalkyl each of no more than 4 carbon atoms;

$R^1$ and $R^2$ are individually hydrogen, alkyl with up to 4 carbon atoms or phenyl; and $R^1$ and $R^2$ together with the two carbon atoms to which they are attached form a fused benzene ring;

$m$ is 1 or 2; and $R^3$ is hydrogen, alkyl of from 1 to 4 carbon atoms, nitro or halogen;

or an agriculturally acceptable salt thereof.

2. Compound as claimed in claim 1 wherein X is hydroxy.

3. Compound as claimed in claim 1 wherein X is OX′ and X′ is sodium, potassium or lithium.

4. Compound as claimed in claim 1 wherein X′ is one equivalent of calcium, magnesium, barium, iron, manganese or zinc.

5. Compound as claimed in claim 1 wherein X′ is straight-chain or branched alkyl of from 1 to 10 carbon atoms, straight-chain or branched alkenyl of from 2 to 6 carbon atoms, straight-chain or branched alkynyl of from 2 to 6 carbon atoms, haloalkyl of from 1 to 3 carbon atoms and 2 to 5 halogen atoms, alkoxyalkyl of from 1 to 4 carbon atoms in the alkylene moiety and 1 to 3 carbon atoms in the alkoxy moiety, or aralkyl of from 1 to 2 carbon atoms in the alkylene moiety and 6 to 10 carbon atoms in the aryl moiety.

6. Compound as claimed in claim 1 wherein R is alkyl of from 1 to 4 carbon atoms or alkoxyalkyl of from 1 to 4 carbon atoms.

7. Compound as claimed in claim 1 wherein $R^1$ and $R^2$ are each hydrogen, straight-chain or branched alkyl of up to 4 carbon atoms or phenyl, or, together with the 2 carbon atoms in the 4- and 5- positions of the imidazole ring, form a fused benzene ring.

8. Compound as claimed in claim 1 wherein $m$ is 1.

9. Compound as claimed in claim 1 wherein $m$ is 2 and each $R^3$ individually is hydrogen, alkyl of up to 4 carbon atoms, nitro, bromine or chlorine.

10. Compound as claimed in claim 1 designated 2-imidazolyl(2′)-carbonylbenzoic acid.

11. Compound as claimed in claim 1 designated 2-imidazolyl(2′)-carbonylbenzoic acid methyl ester.

12. Compound as claimed in claim 1 designated 2-(1′-methoxymethyl)-imidazolyl(2′)-carbonylbenzoic acid methyl ester.

13. Compound as claimed in claim 1 designated 2-imidazolyl(2′)-carbonylbenzoic acid n-butyl ester.

14. Compound as claimed in claim 1 designated 2-imidazolyl(2′)-carbonylbenzoic acid ethyl ester.

15. Compound as claimed in claim 1 designated 2-imidazolyl(2′)-carbonylbenzoic acid hexyl ester.

16. Compound as claimed in claim 1 designated magnesium di[2-imidazolyl-2′-carbonylbenzoate].

17. Compound as claimed in claim 1, wherein X′ in the formula is alkyl of up to 10 carbon atoms or alkenyl of up to 6 carbon atoms, wherein $R^1$ and $R^2$ are, individually, hydrogen or alkyl or, taken together, represent a fused benzene ring, $m$ is 1 and $R^3$ is hydrogen or nitro.

* * * * *